(12) United States Patent
Joe et al.

(10) Patent No.: US 9,321,040 B2
(45) Date of Patent: Apr. 26, 2016

(54) CATALYST FOR GLYCERIN DEHYDRATION, PREPARATION METHOD THEREOF, AND PREPARATION METHOD OF ACROLEIN

(71) Applicant: LG CHEM, LTD., Seoul (KR)

(72) Inventors: Wang Rae Joe, Daejeon (KR); Jun Seon Choi, Daejeon (KR); Ji Yeon Kim, Daejeon (KR); Joo Young Cheon, Daejeon (KR)

(73) Assignee: LG Chem, Ltd., Seoul (KR)

( * ) Notice: Subject to any disclaimer, the term of this patent is extended or adjusted under 35 U.S.C. 154(b) by 0 days.

(21) Appl. No.: 14/442,992

(22) PCT Filed: Jun. 20, 2014

(86) PCT No.: PCT/KR2014/005485
§ 371 (c)(1),
(2) Date: May 14, 2015

(87) PCT Pub. No.: WO2015/046716
PCT Pub. Date: Apr. 2, 2015

(65) Prior Publication Data
US 2015/0336087 A1    Nov. 26, 2015

(30) Foreign Application Priority Data

Sep. 30, 2013 (KR) .................. 10-2013-0116835
May 13, 2014 (KR) .................. 10-2014-0057278

(51) Int. Cl.
 C07C 45/29    (2006.01)
 C07C 45/52    (2006.01)
 B01J 37/00    (2006.01)
 B01J 27/00    (2006.01)
 B01J 27/188   (2006.01)
 B01J 37/08    (2006.01)

(52) U.S. Cl.
CPC ............... B01J 27/188 (2013.01); B01J 37/08 (2013.01); C07C 45/52 (2013.01)

(58) Field of Classification Search
CPC ........... C07C 45/29; C07C 45/52; B01J 37/04; B01J 27/186
USPC .................... 568/486; 502/210, 219
See application file for complete search history.

(56) References Cited

U.S. PATENT DOCUMENTS 8,252,960 B2 *  8/2012  Dubois .............. B01J 27/188
                                                568/485

FOREIGN PATENT DOCUMENTS

| KR | 10-2011-0004872 A | 1/2011 |
| KR | 10-2011-0011603 A | 2/2011 |
| KR | 10-2012-0093853 A | 8/2012 |
| KR | 10-2012-0117254 A | 10/2012 |
| KR | 10-2013-0071224 A | 6/2013 |
| KR | 10-2013-0103639 A | 9/2013 |
| WO | 2009/128555 A     | 10/2009 |

OTHER PUBLICATIONS

Llewelyn, Peter, Supported heteropoly acids for acid catalysed reactions, PH .D, Cardiff University, 2011, Publication No. 516563, pp. 1-161.

* cited by examiner

*Primary Examiner* — Sikarl Witherspoon
(74) *Attorney, Agent, or Firm* — Dentons US LLP

(57) ABSTRACT

The present invention relates to a catalyst for glycerin dehydration, a preparation method thereof, and a preparation method of acrolein, and more particularly, to a catalyst for glycerin dehydration which minimizes by-product formation to improve acrolein selectivity and maintains high catalytic activity during reaction.

17 Claims, No Drawings

US 9,321,040 B2

CATALYST FOR GLYCERIN DEHYDRATION, PREPARATION METHOD THEREOF, AND PREPARATION METHOD OF ACROLEIN

This application is a National Stage Entry of International Application No. PCT/KR2014/005485, filed Jun. 20, 2014, and claims the benefit of Korean Application No. 10-2013-0116835 filed on Sep. 30, 2013, and Korean Application No. 10-2014-0057278 filed on May 13, 2014, all of which are hereby incorporated by reference in their entirety for all purposes as if fully set forth herein.

TECHNICAL FIELD

The present invention relates to a catalyst for glycerin dehydration, a preparation method thereof, and a preparation method of acrolein, and more particularly, to a highly active catalyst for glycerin dehydration which minimizes by-product formation to have high acrolein selectivity, a preparation method thereof, and a preparation method of acrolein.

BACKGROUND OF ART

Acrolein is a simple unsaturated aldehyde compound which includes incomplete reactive groups to have high reactivity, and is used as a major intermediate for synthesis of numerous chemicals. In particular, acrolein has been widely used as an intermediate for synthesis of acrylic acids, acrylic acid esters, superabsorbent polymers, animal feed supplements, or food supplements.

Such acrolein has been mainly prepared by selective gas-phase oxidation of a starting material, propylene, which is obtained during petroleum cracking with atmospheric oxygen. However, as fossil fuels have been reduced and environmental problems such as the greenhouse effect have emerged, many studies have been conducted to develop a method of preparing acrolein using non-fossil fuel-based renewable materials.

Therefore, glycerin, which is a natural by-product obtained from biodiesel production, has received much attention as a raw material for acrolein preparation. In particular, the growth of biodiesel production increases the glycerin market, and industrial application of glycerin has been studied due to its low price.

For example, a method of obtaining acrolein by glycerin dehydration in the presence of a catalyst is known, in which an acid catalyst such as zeolite, phosphate, and tungstophosphoric acid ($H_3PW_{12}O_4$) is used.

However, the previous catalysts used for the preparation of acrolein produce by-products such as hydroxyacetone, hydroxypropanone, propane aldehyde, acetaldehyde, acetone, and polycondensation products of glycerin, and thus there are limitations in their use for the preparation of acrolein with high purity.

Accordingly, there is a demand to develop a highly active catalyst system capable of minimizing by-product formation to increase selectivity and purity of acrolein and improving conversion ratio and reaction yield of glycerin.

DETAILED DESCRIPTION OF THE INVENTION

Technical Problem

An object of the present invention is to provide a highly active catalyst for glycerin dehydration, which is able to minimize by-product formation, thereby increasing selectivity and purity of acrolein.

Another object of the present invention is to provide a preparation method of the catalyst for glycerin dehydration.

Still another object of the present invention is to provide a preparation method of acrolein using the catalyst for glycerin dehydration.

Technical Solution

The present invention provides a catalyst for glycerin dehydration including a heteropolyacid compound containing one or more atoms selected from the group consisting of phosphorus (P) and silicon (Si), and copper (Cu) and tungsten (W).

The present invention provides a preparation method of the catalyst for glycerin dehydration, including the step of sequentially reacting a heteropolyacid compound containing one or more atoms selected from the group consisting of phosphorus (P) and silicon (Si), and tungsten (W), with a barium compound and a copper compound.

Further, the present invention provides a preparation method of acrolein, including the step of reacting glycerin in the presence of the catalyst for glycerin dehydration.

Hereinafter, a catalyst for glycerin dehydration, a preparation method thereof and a preparation method of acrolein according to specific embodiments of the present invention will be described in more detail.

As used herein, the term "glycerin dehydration" means an overall process by which water is separated from a glycerin molecule. Glycerin may be converted to acrolein via this glycerin dehydration.

As used herein, the term "heteropolyacid" means a polyacid having a polynuclear structure in which two or more different kinds of oxo-acids are condensed, and the heteropolyacid may have a soccer ball-shaped structure (Keggin-type) formed by a central atom bound to peripheral atoms.

According to an embodiment of the present invention, a catalyst for glycerin dehydration, including a heteropolyacid compound containing one or more atoms selected from the group consisting of phosphorus (P) and silicon (Si), and copper (Cu) and tungsten (W) is provided.

The present inventors recognized that in the known method of preparing acrolein by gas-phase oxidation of a starting material, propylene has limitations of reduced fossil fuel stocks and environmental problems such as the greenhouse effect, and therefore they have studied on a method of preparing acrolein using environmentally friendly and renewable raw materials. As a result, they found that glycerin dehydration can be performed in the presence of a catalyst including the heteropolyacid compound containing one or more atoms selected from the group consisting of phosphorus and silicon, and copper and tungsten, so as to prepare acrolein with a high yield and a high conversion ratio while minimizing by-product formation, thereby completing the present invention.

The heteropolyacid compound has a soccer ball-shaped structure (Keggin-type) formed by a central phosphorus or silicon atom bound to peripheral oxygen and tungsten atoms, in which copper and/or hydrogen ions are bound between the bound molecules. In particular, the heteropolyacid compound having such a structure is able to regulate the number and strength of Brönsted or Lewis acid sites, leading to more effective glycerin dehydration.

Particularly, the catalyst for glycerin dehydration may exhibit higher acrolein selectivity and lower by-product formation than a catalyst in which $H^+$ cations of a heteropolyacid having a structure of $H_3PW_{12}O_4$ or $H_4SiW_{12}O_4$ are replaced by Cs, Rb, Ca, Fe, Zr, La, Hf, or Bi cations.

In the heteropolyacid compound included in the catalyst for glycerin dehydration, a molar ratio of copper and tungsten may be 1:5 to 1:10,000. The content of oxygen in the heteropolyacid compound may be properly controlled depending on contents of one or more atoms selected from the group consisting of phosphorus and silicon, and tungsten and components further added, and a composition ratio thereof, but the ratio of the number of moles of oxygen to the total number of moles of one or more atoms selected from the group consisting of phosphorus and silicon, and copper and tungsten, may be 2 to 5, preferably 2 to 4. If the oxygen content is too small or too large, the heteropolyacid does not have the soccer ball-shaped (Keggin-type) structure. Therefore, it is preferable that the oxygen content is within the above range.

Further, the heteropolyacid compound may further include one or more second metals selected from the group consisting of Zr, Ti, Ce, V, Nb, Cr, Mo, Mn, Zn, B, and Cu, in addition to one or more atoms selected from the group consisting of phosphorus and silicon, and copper and tungsten. The term "second" is used to distinguish the above metals from phosphorus, silicon, copper, and tungsten, and does not mean the reaction order or priority.

In the heteropolyacid compound, the second metal may bind to share oxygen with one or more atoms selected from the group consisting of phosphorus and silicon, copper, and/or tungsten. The heteropolyacid compound further includes the second metal, thereby improving acrolein selectivity and inhibiting formation of by-products such as hydroxyacetone, hydroxypropanone, etc.

The second metal may be included in an amount of 0.1 mole to 10 moles with respect to tungsten. If the content of the second metal is too small, improvement of the acrolein selectivity may be very slight. Even if the content of the second metal is too large, the increased metal content may not bring out significant improvement in the catalytic activity or selectivity, which is economically unfavorable.

Meanwhile, the heteropolyacid compound may be represented by the following Chemical Formula 1:

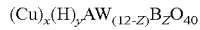   [Chemical Formula 1]

$(Cu)_x(H)_yAW_{(12-z)}B_zO_{40}$ wherein A is phosphorus (P) or silicon (Si), B is selected from the group consisting of Zr, Ti, Ce, V, Nb, Cr, Mo, Mn, Zn, B, and Cu, x is 0.01 to 5, y is 0 to 5, and z is 0 to 12.

Specifically, in the heteropolyacid compound represented by Chemical Formula 1, x corresponding to 0.01 to 5 may vary depending on the replacement amount of hydrogen ions. If X is large, the number of acid sites may be reduced, and if X is small, the number of acid sites may be increased.

When A is phosphorus (P), y may be 3−2x, x may be 0.01 to 1.5, and y may be 0 to 2.98.

Alternatively, when A is silicon (Si), y may be 4−2x, x may be 0.01 to 2, and y may be 0 to 3.98.

In the heteropolyacid compound represented by Chemical Formula 1, $H^+$ cations of the heteropolyacid having a structure of $H_3PW_{12}O_4$ or $H_4SiW_{12}O_4$ are replaced by copper cations. The heteropolyacid may be prepared by a preparation method of the catalyst for glycerin dehydration described below. In particular, the copper ions may function to control the acid strength to be suitable for the acrolein production reaction by increasing distribution of relatively weak acid sites and decreasing strong acid sites, and thus the catalyst may exhibit higher selectivity than a catalyst in which hydrogen ions are replaced by Cs, Rb, Ca, Fe, Zr, La, Hf, or Bi atoms.

Meanwhile, specific examples of the heteropolyacid compound represented by Chemical Formula 1 may include $Cu_{0.25}H_{2.5}PW_{12}O_{40}$, $Cu_{0.5}H_{2.0}PW_{12}O_{40}$, $Cu_{0.75}H_{1.5}PW_{12}O_{40}$, $Cu_{1.0}H_{1.0}PW_{12}O_{40}$, $Cu_{1.5}PW_{12}O_{40}$, $Cu_{0.75}H_{2.5}SiW_{12}O_{40}$, $Cu_{0.75}H_{1.5}PMo_{12}O_{40}$, $Cu_{0.75}H_{2.5}SiMo_{12}O_{40}$, $Cu_{0.75}H_{1.5}PW_6Mo_6O_{40}$, etc.

The catalyst for glycerin dehydration may further include a support onto which the heteropolyacid compound is immobilized. Any support that is known to be used in a typical catalyst may be used without limitations. Specific examples of the support may include silica, alumina, silica-alumina, titania, zeolite, activated carbon, clay, zirconia, magnesia, magnesium aluminate, calcium aluminate, silicon carbide, zirconium phosphate, or mixtures thereof. Preferably, silica having a pore size of 20 nm or more may be used.

The support may function to immobilize the heteropolyacid compound containing one or more atoms selected from the group consisting of phosphorus and silicon, and copper and tungsten, and the heteropolyacid compound may be immobilized on the support with a large surface area by sharing oxygen therewith. When the heteropolyacid compound is prepared by immobilizing it on the support, it is easier to store and transport, and a large amount of glycerin may be effectively reacted due to the large surface area.

The support may have a specific surface area of 10 to 500 m²/g, and preferably 50 to 200 m²/g. In particular, the catalyst for glycerin dehydration prepared by supporting the heteropolyacid compound on the support having a large specific surface area within the above range has a proper pore size, thereby reducing coke deposition and providing sufficient catalytic activity.

The catalyst for glycerin dehydration may include 1 to 50 parts by weight of the heteropolyacid compound containing one or more atoms selected from the group consisting of phosphorus and silicon, and copper and tungsten, based on 100 parts by weight of the support.

According to another embodiment of the present invention, a preparation method of the catalyst for glycerin dehydration including the step of sequentially reacting the heteropolyacid compound containing one or more atoms selected from the group consisting of phosphorus (P) and silicon (Si), and tungsten (W), with a barium compound and a copper compound is provided.

This preparation method may be used to provide the above-described catalyst for glycerin dehydration of an embodiment of the present invention. As described above, this catalyst is able to minimize by-product formation during glycerin dehydration, thereby preparing acrolein with high selectivity.

In more detail, the catalyst for glycerin dehydration may be prepared by a step of reacting the heteropolyacid compound represented by the following Chemical Formula 2 with the barium compound to prepare a compound of the following Chemical Formula 3, and a step of reacting the prepared compound of Chemical Formula 3 with the copper compound to prepare a compound of the following Chemical Formula 1.

   [Chemical Formula 1]

$(Cu)_x(H)_yAW_{(12-z)}B_zO_{40}$

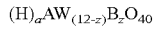   [Chemical Formula 2]

$(H)_aAW_{(12-z)}B_zO_{40}$

   [Chemical Formula 3]

$(Ba)_x(H)_yAW_{(12-z)}B_zO_{40}$

Herein, A is phosphorus (P) or silicon (Si), B is selected from the group consisting of Zr, Ti, Ce, V, Nb, Cr, Mo, Mn, Zn, B, and Cu, x is independently 0.01 to 5, y is independently 0 to 5, z is 0 to 12, and a is 0.01 to 5.

In Chemical Formulae 1 and 3, when A is phosphorus (P), y may be 3−2x, x may be 0.01 to 1.5, and y may be 0 to 2.98, and when A is silicon (Si), y may be 4−2x, x may be 0.01 to 2, and y may be 0 to 3.98.

The step of preparing the compound of Chemical Formula 3 and the step of preparing the compound of Chemical Formula 1 may be performed in the presence of a solvent. That is, the compound of Chemical Formula 2 and the barium compound may be reacted in the presence of a solvent, and the prepared compound of Chemical Formula 3 and the copper compound may be reacted in the presence of a solvent. Examples of the solvent may include water, alcohols, or mixtures thereof.

As the barium compound, $Ba(OH)_2$, $BaSO_4$, $Ba(NO_3)_2$, $BaCO_3$, $BaCl_2$, or a mixture thereof may be used. In particular, when $Ba(OH)_2$ is used, water rather than a strong acid such as sulfuric acid or nitric acid is produced as a by-product, thus activity of the catalyst prepared is not affected thereby, and a catalyst purification process is not necessary. Therefore, it is possible to prepare the catalyst for glycerin dehydration in an easier manner.

Further, as the copper compound, $CuSO_4$, $Cu(NO_3)_2$, $CuCO_3$, $CuCl_2$, or a mixture thereof may be used. Of the copper compounds, when $CuSO_4$ is used, $BaSO_4$ produced during replacement is insoluble and thus is precipitated. Therefore, it is easy to separate the precipitates.

The preparation method of the catalyst for glycerin dehydration may further include the step of drying and calcinating the compound of Chemical Formula 1 which is prepared by the step of sequentially reacting the heteropolyacid compound with the barium compound and the copper compound.

In more detail, in the drying step, the heteropolyacid compound is reacted with the copper compound, and then dried at 100° C. or higher for 10 minutes to 24 hours to remove the solvent before calcination. In this drying process, a drying method and a drying device which are known to be typically used may be used, and for example, a heat source such as a hot air dryer, an oven, a heating plate, etc. may be used to perform the drying process.

Further, the calcinating step means a process of preparing a curable material by heating a reactant at a high temperature, and may be performed at a temperature ranging from 100 to 900° C., preferably from 200to 500° C. At a lower temperature than the above range, organic materials remaining in the catalyst are not properly removed to reduce intrinsic activity of the catalyst. At a higher temperature than the above range, the structure of heteropolyacid is broken, leading to loss of the intrinsic properties of the acid.

The drying and calcinating steps may be performed for 10 minutes to 10 hours, respectively. If the drying and calcinating times are too short, the catalyst may not be completely dried and calcined, and if the drying and calcinating times are too long, various side reactions such as carbonization of the catalyst may occur.

Meanwhile, prior to the steps of drying and calcinating the compound of Chemical Formula 1, a step of separating a precipitate of the barium compound, which is produced by sequentially reacting the compound of Chemical Formula 2 with the barium compound and the copper compound, may be further included. The step of separating the precipitate is to remove the barium precipitate as a replacement by-product from a solution, in which the compound of Chemical Formula 1 produced by sequentially reacting the compound of Chemical Formula 2 with the barium compound and the copper compound is dissolved. The precipitate may be separated and removed by filtration or centrifugation.

The preparation method of the catalyst for glycerin dehydration of an embodiment may further include a step of supporting the compound of Chemical Formula 1 on a support. The step of supporting the compound on the support may be performed by any method known in the art without limitation, and for example, an impregnation method or a powder mixing method may be used. Further, the above descriptions may also be applied to a specific example of the support and a mixing ratio thereof without limitation.

The impregnation method is a process of using the support powder as it is, or preparing the powder in the form of spheres or pellets, and then aging and calcinating the support with the mixture containing the gel-type precipitate. The powder mixing method is a process of calcinating and supporting a mixture which is obtained by mixing the powdery support with the powdery resultant from the aging and drying processes in the preparation process of the oxide catalyst.

In particular, the impregnation method is more preferably applied to the catalyst for glycerin dehydration of an embodiment, because it is easy to disperse the heteropolyacid compound on the support. In the impregnation method, a polar solvent including water, alcohols such as methanol, THF, acetone, or acetonitrile may be used as a solvent. In particular, if water or alcohol such as methanol is used as a supporting solvent, the catalyst for glycerin dehydration to be prepared may exhibit higher catalytic activity.

According to still another embodiment of the present invention, a preparation method of acrolein including the step of reacting glycerin in the presence of the above-described catalyst for glycerin dehydration is provided.

As described above, when the catalyst for glycerin dehydration of an embodiment of the present invention may be used, it is possible to perform glycerin dehydration with high acrolein selectivity, in particular, to minimize by-product formation, compared to use of the previously known catalysts.

The amount of the catalyst for glycerin dehydration may be properly controlled depending on the amount and concentration of the reactant glycerin, and for example, the catalyst may be packed at a weight hourly space velocity of 10 to 300 mmol/h·$g_{cat}$, and preferably, at a weight hourly space velocity of 10 to 100 mmol/h·$_{cat}$.

Further, the step of reacting glycerin may be performed at a temperature of 200 to 400° C. Since the step of reacting glycerin is an endothermic reaction, the reaction may be preferably performed at a temperature within the above range in order to prepare acrolein with high conversion ratio and selectivity.

Advantageous Effects

According to the present invention, a highly active catalyst for glycerin dehydration which minimizes by-product formation to have high acrolein selectivity, a preparation method thereof, and a preparation method of acrolein using the same are provided.

DETAILED DESCRIPTION OF THE EMBODIMENTS

The present invention will be described in more detail with reference to the following examples. However, these examples are for illustrative purposes only, and the invention is not intended to be limited by these examples.

EXAMPLES AND COMPARATIVE EXAMPLES

Preparation of Catalyst for Glycerin Dehydration

Example 1

4 g of tungstophosphoric acid ($H_3PW_{12}O_{40}$, WAKO Co.) was diluted in 30 ml of distilled water to prepare a tungstophosphoric acid aqueous solution. 0.109 g of barium hydroxide ($Ba(OH)_2.8H_2O$, purity 98%, KANTO Co.) was added to the tungstophosphoric acid aqueous solution. The solution was left until a clear $Ba_{0.25}H_{2.5}PW_{12}O_{40}$ aqueous solution was obtained by complete replacement of barium hydroxide, and then 0.087 g of copper sulfide ($CuSO_4.5H_2O$, purity 99%, DAEJUNG) was dissolved in 10 ml of distilled water in a separate beaker to prepare a copper sulfide aqueous solution. Thereafter, the copper sulfide aqueous solution thus prepared was slowly added to the $Ba_{0.25}H_{2.5}PW_{12}O_{40}$ aqueous solution, followed by stirring. Finally, a $Cu_{0.25}H_{2.5}PW_{12}O_{40}$ aqueous solution and $BaSO_4$ precipitate were obtained. The produced $BaSO_4$ was removed by centrifugation, and the resulting $Cu_{0.25}H_{2.5}PW_{12}O_{40}$ aqueous solution was heated to remove distilled water, and then dried in an oven at 110° C. for 12 hours and calcined at 300° C. for 4 hours to prepare a $Cu_{0.25}H_{2.5}PW_{12}O_{40}$ catalyst.

Example 2

A $Cu_{0.5}H_{2.0}PW_{12}O_{40}$ catalyst was prepared in the same manner as in Example 1, except that 0.219 g of barium hydroxide and 0.173 g of copper sulfide were used.

Example 3

A $Cu_{0.75}H_{1.5}PW_{12}O_{40}$ catalyst was prepared in the same manner as in Example 1, except that 0.329 g of barium hydroxide and 0.260 g of copper sulfide were used.

Example 4

A $Cu_{1.0}H_{1.0}PW_{12}O_{40}$ catalyst was prepared in the same manner as in Example 1, except that 0.438 g of barium hydroxide and 0.347 g of copper sulfide were used.

Example 5

A $Cu_{1.5}PW_{12}O_{40}$ catalyst was prepared in the same manner as in Example 1, except that 0.657 g of barium hydroxide and 0.520 g of copper sulfide were used.

Example 6

4 g of tungstosilicic acid ($H_4SiW_{12}O_{40}$, WAKO Co.) was diluted in 30 ml of distilled water to prepare a tungstosilicic acid aqueous solution. 0.286 g of barium hydroxide ($Ba(OH)_2.8H_2O$, purity 98%, KANTO Co.) was added to the tungstosilicic acid aqueous solution. The solution was left until a clear $Ba_{0.75}H_{2.5}SiW_{12}O_{40}$ aqueous solution was obtained by complete replacement of barium hydroxide, and then 0.226 g of copper sulfide ($CuSO_4.5H_2O$, purity 99%, DAEJUNG) was dissolved in 10 ml of distilled water in a separate beaker to prepare a copper sulfide aqueous solution. Thereafter, the copper sulfide aqueous solution thus prepared was slowly added to the $Ba_{0.75}H_{2.5}SiW_{12}O_{40}$ aqueous solution, followed by stirring. Finally, a $Cu_{0.75}H_{2.5}SiW_{12}O_{40}$ aqueous solution and $BaSO_4$ precipitate were obtained. The produced $BaSO_4$ was removed by centrifugation, and the resulting $Cu_{0.75}H_{2.5}SiW_{12}O_{40}$ aqueous solution was heated to remove distilled water, and then dried in an oven at 110° C. for 12 hours and calcined at 300° C. for 4 hours to prepare a $CU_{0.75}H_{2.5}SiW_{12}O_{40}$ catalyst.

Example 7

0.2 g of the catalyst prepared in Example 3 was dissolved in 7 ml of distilled water to prepare an aqueous solution. Then, 1.8 g of silica (Q30, FUJI Co.) was added thereto to prepare a silica slurry, followed by stirring. Thereafter, water was removed from the silica slurry using a rotary evaporator. The slurry was dried in an oven at 110° C. for 12 hours and calcined at 300° C. for 4 hours to prepare a $Cu_{0.75}H_{1.5}PW_{12}O_{40}/SiO_2$ (Q30) catalyst supported at a weight ratio of 1:10.

Example 8

A $Cu_{0.75}H_{1.5}PW_{12}O_{40}/SiO_2$—$Al_2O_3$ supported catalyst was prepared in the same manner as in Example 7, except that $SiO_2$—$Al_2O_3$ (ALDRICH Co.) was used as a support instead of silica (Q30, FUJI Co.).

Example 9

A $Cu_{0.75}H_{1.5}PW_{12}O_{40}/ST$ supported catalyst was prepared in the same manner as in Example 7, except that ST31116 (SAINT GOBAIN's $TiO_2$) was used as a support instead of silica (Q30, FUJI Co.).

Comparative Example 1

$H_3PW_{12}O_{40}$ purchased from WAKO Co. was used.

Comparative Example 2

$H_4SiW_{12}O_{40}$ purchased from WAKO Co. was used.

Comparative Example 3

A $Cs_{2.5}H_{0.5}PW_{12}O_{40}$ catalyst was prepared in the similar manner as in Example 1, except that cesium nitrate was used.

Comparative Example 4

A $H_3PW_{12}O_{40}/SiO_2$ catalyst was prepared in the same manner as in Example 7, except that $H_3PW_{12}O_{40}$ (WAKO Co.) was used instead of $Cu_{0.75}H_{1.5}PW_{12}O_{40}$.

Comparative Example 5

A $H_4SiW_{12}O_{40}/SiO_2$—$Al_2O_3$ catalyst was prepared in the same manner as in Example 8, except that $H_4SiW_{12}O_{40}$ (WAKO Co.) was used instead of $Cu_{0.75}H_{1.5}PW_{12}O_{40}$.

Comparative Example 6

A $H_4SiW_{12}O_{40}/TiO_2$ catalyst was prepared in the same manner as in Comparative Example 5, except that $TiO_2$ (DEGUSSA Co.) was used as a support.

Experimental Example

Conversion Ratio of Glycerin, Selectivity of Acrolein and By-Product

An HTS (high-throughput screening) facility which was manufactured to evaluate performance using a small amount of the catalyst prepared in the example or comparative examples in a short time under conditions given in the following Table 1 was used to prepare acrolein from glycerin, and the product was subjected to in-situ GC analysis to calculate conversion ratio, selectivity, and yield. The glycerin conversion ratio and acrolein selectivity are given in the following Tables 2 and 3.

Here, the glycerin conversion ratio represents a ratio of glycerin to converted compounds, and the acrolein selectivity represents a ratio of acrolein to the converted compounds.

Further, comparative selectivity 1 represents a comparison of hydroxyacetone selectivity to acrolein selectivity and molecular weight 130 compound selectivity, and comparative selectivity 2 represents a comparison of by-product selectivity to acrolein selectivity and molecular weight 130 compound selectivity. In comparative selectivity 1 or 2, hydroxyacetone is a major by-product in glycerin dehydration, and the by-product includes hydroxyacetone, aryl alcohol, acetol, propionic acid, 1,2-propanediol, 1,3-propanediol, or cyclic acetal compounds produced by dimer dehydration between glycerin molecules or acetol and glycerin. In the molecular weight 130 compound selectivity, the molecular weight 130 compound is a cyclic acetal compound produced by dehydration of acrolein and glycerin, and is a by-product produced from the bottom of reactor when heated to 200° C.

TABLE 1

| Conditions for glycerin dehydration | |
|---|---|
| Reaction pressure | 1 atm |
| Reaction temperature | 280° C. |
| Feed rate of reactant | 3.5 ml/h |
| Reaction time | 1 h |
| Glycerin concentration | 28.08 wt % |
| WHSV (weight hourly space velocity) | 113.03 mmol/(h · $g_{cat}$) |
| Catalyst amount | 0.1 g |

TABLE 2

Chemical Formula of catalysts prepared in examples and comparative examples, and glycerin conversion ratio and selectivity

| Example | Chemical Formula | Glycerin conversion ratio (%) | Acrolein selectivity (%) | Molecular weight 130 selectivity (%) |
|---|---|---|---|---|
| Example 1 | $Cu_{0.25}H_{2.5}PW_{12}O_{40}$ | 4.52 | 16.69 | 23.48 |
| Example 2 | $Cu_{0.5}H_{2.0}PW_{12}O_{40}$ | 11.91 | 13.39 | 28.18 |
| Example 3 | $Cu_{0.75}H_{1.5}PW_{12}O_{40}$ | 8.12 | 30.69 | 15.17 |
| Example 4 | $Cu_{1.0}H_{1.0}PW_{12}O_{40}$ | 6.96 | 6.47 | 28.26 |
| Example 5 | $Cu_{1.5}PW_{12}O_{40}$ | 17.61 | 7.49 | 28.86 |
| Example 6 | $Cu_{0.75}H_{2.5}SiW_{12}O_{40}$ | 15.2 | 10.6 | 10.88 |
| Example 7 | $Cu_{0.75}H_{1.5}PW_{12}O_{40}/SiO_2(Q30)$ | 22.86 | 19.39 | 9.4 |
| Example 8 | $Cu_{0.75}H_{1.5}PW_{12}O_{40}/SiO_2—Al_2O_3$ | 30.84 | 12.10 | 1.59 |
| Example 9 | $Cu_{0.75}H_{1.5}PW_{12}O_{40}/ST$ | 10.81 | 24.54 | 4.79 |
| Comparative Example 1 | $H_3PW_{12}O_{40}$ | 4.22 | 3.98 | 24.73 |
| Comparative Example 2 | $H_4SiW_{12}O_{40}$ | 3.9 | 6.1 | 20.28 |
| Comparative Example 3 | $Cs_{2.5}H_{0.5}PW_{12}O_{40}$ | 1.33 | 13.32 | 11.77 |
| Comparative Example 4 | $H_3PW_{12}O_{40}/SiO_2$ | 16.29 | 12.27 | 4.21 |
| Comparative Example 5 | $H_4SiW_{12}O_{40}/SiO_2—Al_2O_3$ | 18.01 | 11.44 | 2.96 |
| Comparative Example 6 | $H_4SiW_{12}O_{40}/TiO_2$ | 9.46 | 13.94 | 10.06 |

TABLE 3

Selectivity and comparative selectivity of hydroxyacetone

| Example | Hydroxy-acetone selectivity (%) | *Comparative selectivity 1 | **Comparative selectivity 2 |
|---|---|---|---|
| Example 1 | 5.57 | 0.22 | 2.16 |
| Example 2 | 15.58 | 0.33 | 3.07 |
| Example 3 | 10.47 | 0.29 | 1.37 |
| Example 4 | 12.52 | 0.73 | 3.56 |
| Example 5 | 3.30 | 0.18 | 3.15 |
| Example 6 | 9.90 | 0.67 | 4.28 |
| Example 7 | 5.57 | 1.29 | 2.80 |
| Example 8 | 22.90 | 1.80 | 6.35 |
| Example 9 | 28.51 | 1.08 | 2.35 |
| Comparative Example 1 | 16.05 | 1.20 | 5.15 |
| Comparative Example 2 | 20.79 | 1.68 | 5.33 |
| Comparative Example 3 | 21.31 | 1.21 | 3.92 |
| Comparative Example 4 | 19.51 | 1.41 | 5.33 |
| Comparative Example 5 | 24.60 | 2.15 | 7.11 |
| Comparative Example 6 | 24.36 | 1.75 | 5.66 |

*Comparative selectivity 1 = hydroxyacetone selectivity/(acrolein selectivity + molecular weight 130 compound selectivity)
**Comparative selectivity 2 = by-product selectivity/(acrolein selectivity + molecular weight 130 compound selectivity)

As shown in Tables 2 and 3, when the catalysts including phosphorus and/or silicon, and copper and tungsten of the examples were used to react glycerin, high glycerin conversion ratio and acrolein selectivity were observed, compared to use of the catalysts of the comparative examples, and comparative selectivity 1 or 2 which are ratios of by-product selectivity to selectivity of acrolein which is a main product as a target of the reaction was low, compared to use of the catalysts of the comparative examples.

According to the experimental results, in particular, the catalysts prepared in the examples exhibited higher acrolein selectivity and lower by-product selectivity than those prepared by using the heteropolyacid compound of $H_3PW_{12}O_4$ and by replacing hydrogens of the heteropolyacid compound with Cs in Comparative Example 3.

The invention claimed is:

1. A catalyst for glycerin dehydration, comprising a heteropolyacid compound represented by Chemical Formula 1:

$$(Cu)_x(H)_y AW_{(12-z)}B_z O_{40}$$ [Chemical Formula 1]

wherein A is phosphorus (P) or silicon (Si),
B is selected from the group consisting of Zr, Ti, Ce, V, Nb, Cr, Mo, Mn, Zn, B, and Cu,
X is 0.01 to 5,
y is 0 to 5, and
z is 0 to 12.

2. The catalyst for glycerin dehydration of claim 1, wherein when A is phosphorus (P), y is 3−2x, x is 0.01 to 1.5, and y is 0 to 2.98.

3. The catalyst for glycerin dehydration of claim 1, wherein when A is silicon (Si), y is 4−2x, x is 0.01 to 2, and y is 0 to 3.98.

4. The catalyst for glycerin dehydration of claim 1, further comprising a support onto which the heteropolyacid compound is immobilized.

5. The catalyst for glycerin dehydration of claim 4, wherein the support is selected from the group consisting of silica, alumina, silica-alumina, titania, zeolite, activated carbon, clay, zirconia, magnesia, magnesium aluminate, calcium aluminate, silicon carbide, zirconium phosphate, or mixtures thereof.

6. The catalyst for glycerin dehydration of claim 4, wherein the support has a specific surface area (BET) of 10 to 500 m$^2$/g.

7. The catalyst for glycerin dehydration of claim 4, comprising 1 to 50 parts by weight of the heteropolyacid compound, based on 100 parts by weight of the support.

8. A preparation method of a cataylst for glycerin dehydration, comprising the steps of:
reacting a heteropolyacid compound represented by Chemical Formula 2 with a barium compound to prepare a compound of Chemical Formula 3; and
reacting the prepared compound of Chemical Formula 3 with a copper compound to prepare a compound of Chemical Formula 1:

$$(Cu)_x(H)_y AW_{(12-z)}B_z O_{40}$$ [Chemical Formula 1]

$$(H)_a AW_{(12-z)}B_z O_{40}$$ [Chemical Formula 2]

$$(Ba)_x(H)_y AW_{(12-z)}B_z O_{40}$$ [Chemical Formula 3]

wherein A is phosphorus (P) or silicon (Si),
B is selected from the group consisting of Zr, Ti, Ce, V, Nb, Cr, Mo, Mn, Zn, B, and Cu,
x is independently 0.01 to 5,
y is independently 0 to 5,
z is 0 to 12, and
a is 0.01 to 5.

9. The preparation method of claim 8, wherein the barium compound includes one or more selected from the group consisting of Ba(OH)$_2$, BaSO$_4$, Ba(NO$_3$)$_2$, BaCO$_3$, and BaCl$_2$.

10. The preparation method of claim 8, wherein the copper compound is CuSO$_4$, Cu(NO$_3$)$_2$, CuCO$_3$, or CuCl$_2$.

11. The preparation method of claim 8, wherein the step of preparing the compound of Chemical Formula 3 and the step of preparing the compound of Chemical Formula 1 are performed in the presence of a solvent.

12. The preparation method of claim 8, further comprising the step of drying and calcinating the compound of Chemical Formula 1.

13. The preparation method of claim 12, wherein the calcinating step is performed at a temperature ranging from 100 to 900° C.

14. The preparation method of claim 8, further comprising the step of supporting the compound of Chemical Formula 1 on a support.

15. A preparation method of acrolein, comprising the step of reacting glycerin in the presence of the catalyst for glycerin dehydration of claim 1.

16. The preparation method of claim 15, wherein the catalyst for glycerin dehydration is packed at a weight hourly space velocity of 10 to 300 mmol/h·g$_{cat}$.

17. The preparation method of claim 15, wherein the step of reacting glycerin is performed at a temperature of 200 to 400° C.

* * * * *